(12) United States Patent
Balligand et al.

(10) Patent No.: US 9,696,324 B2
(45) Date of Patent: Jul. 4, 2017

(54) METHOD FOR MEASURING NITRIC OXIDE IN BLOOD

(71) Applicant: L'UNIVERSITÉ CATHOLIQUE DE LOUVAIN, Louvain-la-Neuve (BE)

(72) Inventors: Jean-Luc Balligand, Kraainem (BE); Irina Lobysheva, Auderghem (BE)

(73) Assignee: L'UNIVERSITÉ CATHOLIQUE DE LOUVAIN, Louvain-la-Neuve (BE)

( * ) Notice: Subject to any disclaimer, the term of this patent is extended or adjusted under 35 U.S.C. 154(b) by 0 days.

(21) Appl. No.: 14/367,209

(22) PCT Filed: Dec. 26, 2012

(86) PCT No.: PCT/EP2012/076904
§ 371 (c)(1),
(2) Date: Jun. 19, 2014

(87) PCT Pub. No.: WO2013/098294
PCT Pub. Date: Jul. 4, 2013

(65) Prior Publication Data
US 2014/0336534 A1    Nov. 13, 2014

(30) Foreign Application Priority Data

Dec. 27, 2011    (EP) .................................... 11195797

(51) Int. Cl.
*G01N 33/72*    (2006.01)
*G01N 33/84*    (2006.01)
(Continued)

(52) U.S. Cl.
CPC ....... *G01N 33/721* (2013.01); *A61B 5/15003* (2013.01); *A61B 5/154* (2013.01);
(Continued)

(58) Field of Classification Search
CPC .... G01R 33/60; G01N 33/0037; G01N 33/84; G01N 33/721; G01N 33/4925; A61B 5/150755
(Continued)

(56) References Cited

U.S. PATENT DOCUMENTS

| 6,436,705 B1 * | 8/2002 | Bakaltcheva | ........ | A01N 1/0221 435/366 |
| 2003/0095890 A1 * | 5/2003 | Miekka | ............ | A61K 39/39591 422/22 |

(Continued)

OTHER PUBLICATIONS

International Search Report and Written Opinion of the International Searching Authority for International Application No. PCT/EP2012/076904, mailed on Jan. 31, 2013.
(Continued)

*Primary Examiner* — Rebecca M Fritchman
(74) *Attorney, Agent, or Firm* — Knobbe, Martens, Olson & Bear LLP

(57) ABSTRACT

The present invention provides a method for the quantification of NO in a blood sample comprising the steps of collecting a blood sample, dividing said collected blood sample into three blood subsamples, chemically treating one blood subsample with an antioxidant to at least partly reduce free radicals of said blood subsample, performing EPR measurement of said blood subsamples, performing a first comparison of said chemically treated blood subsample EPR measurement with the EPR measurement of a non-chemically treated blood sub-sample thereby obtaining a first comparison result and performing a second comparison of this result with an EPR measurement of the remaining blood subsample in order to eliminate background signals.

17 Claims, 13 Drawing Sheets

(51) Int. Cl.
  *G01R 33/60* (2006.01)
  *G01N 33/49* (2006.01)
  *A61B 5/15* (2006.01)
  *A61B 5/154* (2006.01)
  *G01N 33/00* (2006.01)

(52) U.S. Cl.
  CPC .... *A61B 5/15074* (2013.01); *A61B 5/150732* (2013.01); *A61B 5/150755* (2013.01); *G01N 33/4925* (2013.01); *G01N 33/84* (2013.01); *G01R 33/60* (2013.01); *G01N 33/0037* (2013.01)

(58) Field of Classification Search
  USPC ............................................ 600/573; 33/573
  See application file for complete search history.

(56) References Cited

U.S. PATENT DOCUMENTS

2009/0223080 A1* 9/2009 McCarthy .......... A61B 19/0248
  34/284
2011/0210737 A1* 9/2011 Tseitlin .............. G01R 33/1284
  324/316

OTHER PUBLICATIONS

Hogg, "Detection of nitric oxide by electron paramagnetic resonance spectroscopy," *Free Radical Biology & Medicine,* vol. 49, pp. 122-129 (2010).
Tsuchiya et al., "New Methods to Evaluate Endothelial Function: Evaluation of Endothelial Function by Hemoglobin-Nitric Oxide Complex Using Electron Paramagnetic Resonance Spectroscopy," *Journal of Pharmacological Sciences,* vol. 93, pp. 417-422 (2003).

* cited by examiner

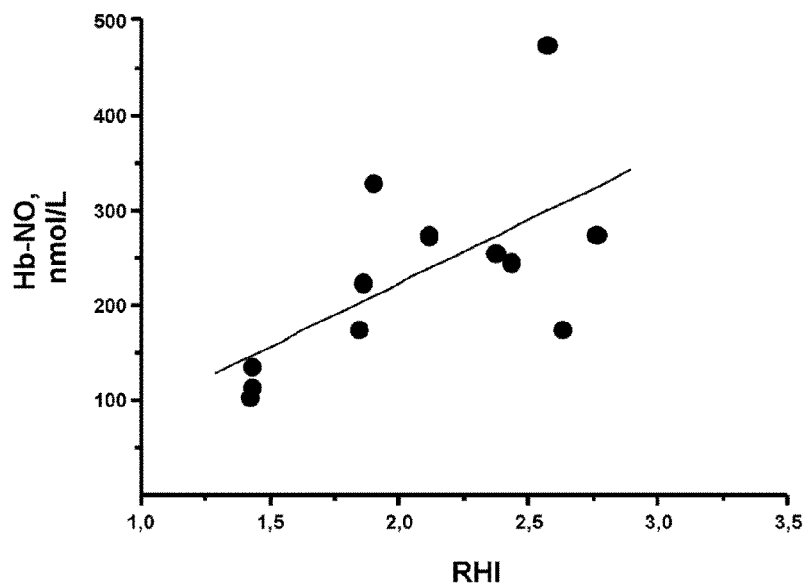
FIG. 4
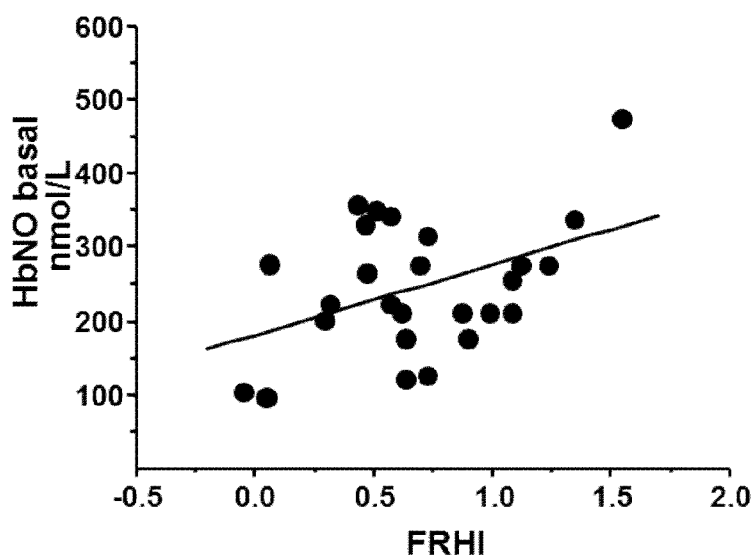
FIG. 4-I

A

B

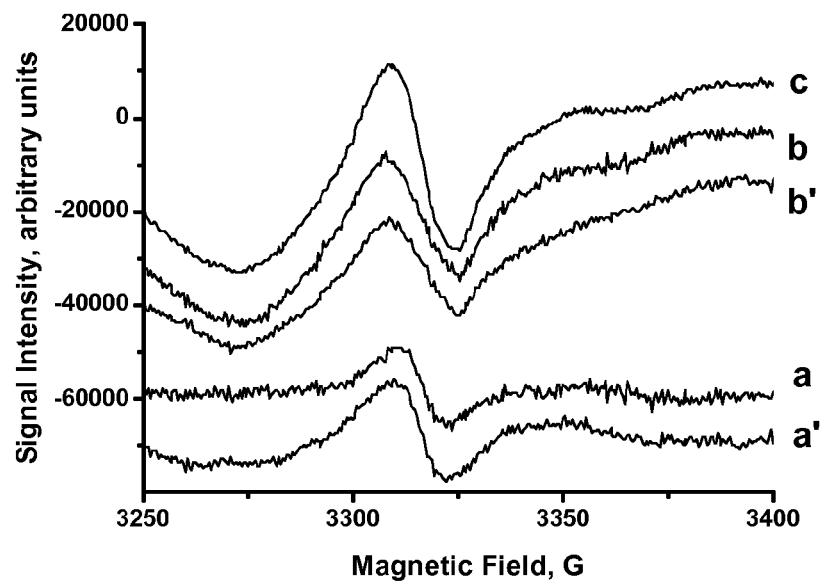
FIG. 7-IA
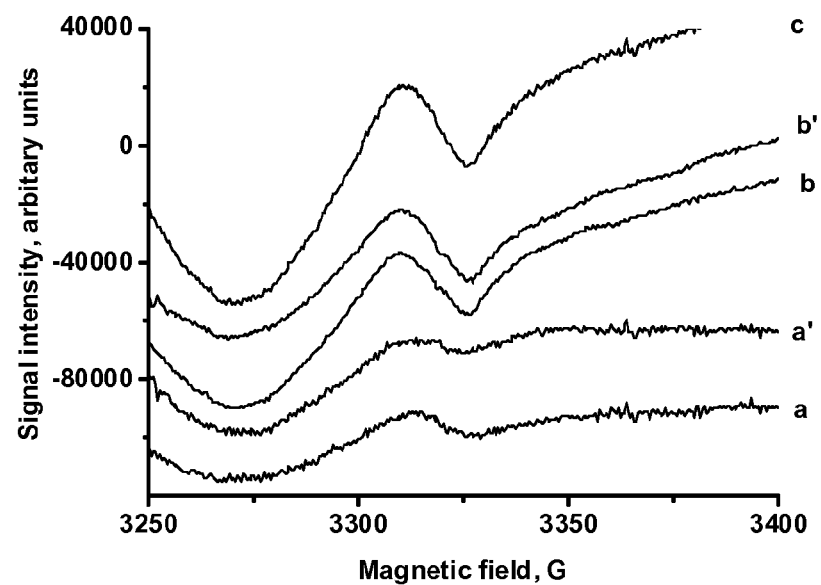
FIG. 7-IB

METHOD FOR MEASURING NITRIC OXIDE IN BLOOD

CROSS-REFERENCE TO RELATED APPLICATIONS

This application is the U.S. National Phase under 35 U.S.C. §371 of International Application PCT/EP2012/076904, filed Dec. 26, 2012, which claims priority to EP 11195797.3, filed Dec. 27, 2011.

FIELD OF THE INVENTION

The present invention relates to the measurement of nitric oxide (NO) amounts accumulated in blood. More precisely, the present invention relates to the measurement of NO amounts accumulated in vivo in blood using electron paramagnetic resonance (EPR).

BACKGROUND

Nitric oxide is a paramagnetic molecule. The detection of NO in biological tissues and liquids is a challenge because of its low concentration and small half-life.

A proper assay of the level of bioavailable nitric oxide in vivo in human circulation is important for the protection of human health. Insufficiency of NO production from the endothelium is a crucial sign of endothelial dysfunction in many metabolic diseases and, especially, cardiovascular diseases developed under various risk factors including age, hypertension, smoking, and hypercholesterolemia. The functionality of the endothelial nitric oxide synthase (eNOS) and NO bioavailability in the vascular bed in vivo are difficult to assess quantitatively, especially in humans.

Invasive and non-invasive methods were developed to indirectly determine the level of bioavailable NO and study its dynamics. The level of eNOS expression, the phosphorylation status of eNOS and eNOS activity can be studied ex vivo in biopsy samples from isolated vessels and tissues. However, this analysis cannot characterize NO bioavailability in vivo.

NO can be converted into nitrite and nitrate in reactions with various specific and non-specific targets. Therefore, measurements of nitrite/nitrate ($NO_x$) concentration in extracellular fluids such as blood plasma have been widely used in different laboratories. The Griess reaction detects nitrite based on its reaction with sulphanilic acid. The reaction product is then detected by spectrophotometry. The chemiluminescence technique provides higher sensitivity using back-reduction of nitrite/nitrate to NO in a reflux chamber at 95° C. Both techniques allow nitrite/nitrate detection in biological samples, however, proper data interpretation is difficult due to the dietary variability and the active nitrite/nitrate metabolism. Moreover, peroxynitrite, a strong oxidant produced by the reaction of superoxide anions and NO and detected at high level in pathophysiological models, is also converted to $NO_x$ as end product.

The level of NO production can be detected amperometrically by NO-specific electrodes. The method requires catheterization in order to insert the electrode close to the endothelium, which is very fragile and can be damaged by this invasive procedure and the application of the method is limited by the sensitivity/specificity of the signal depending on the sensor.

EndoPAT is a standardized device for non-invasive endothelial function assessment. The technology is based on the detection of peripheral arterial tone signal using volume-sensitive sensors placed on the fingertips. As the endothelial vasodilation is mediated by several other factors besides NO, the EndoPAT method can only be used as an indirect assessment of endothelial NO production.

Nitric oxide is known to bind tightly to hemoglobin (Hb). Interactions of NO with Hb are believed to be a major route of NO metabolism in the vascular bed. It follows that the levels of Hb-NO in blood are an excellent indication of endogenous NO production.

Distinct forms of paramagnetic heme-NO adducts can be formed depending on NO hosting at α- or β-subunits and the Hb conformation state under variation of oxygen pressure and allosteric factor abundance in erythrocytes. Actually, three forms of nitrosylated Hb with the same principal g-values ($g_{xx}$=2.08, $g_{yy}$=2.04, and $g_{zz}$=2.01) can be observed in erythrocytes in human blood: i) 5-coordinated nitrosylated α-Hb (T-form, deoxy-like); ii) 6-coordinated nitrosylated α-Hb (R-form, oxy-like); iii) 6-coordinated nitrosylated β-Hb (R-form, oxy-like). Remarkably, the EPR spectrum of T-form (deoxy-like) displays the well-resolved hyperfine structure ($A_z^{hfs}$=16.8 G) due to the net donation of electron density from Fe(II) to NO after cleavage of the bond between iron and proximal His of the R form. Moreover, the dissociation rate constant was also found to be much higher for the T-form than for the R-form (with a resulting $t_{1/2}$~15 minutes and 20 hours, respectively). This highlights the interest to follow the evolution of the T-form in venous blood as a dynamic marker of NO availability in the systemic circulation.

Electron Paramagnetic Resonance (EPR) is a method for the individual detection of the level of various paramagnetic compounds in biological samples. EPR is an extremely attractive technique to analyze NO bioavailability. Measurement of paramagnetic hemoglobin-nitric oxide adducts (Hb-NO) in whole blood and erythrocytes by the EPR spectroscopy was proposed in the last decade in animal models and human blood. Unique information about systemic NO levels could be obtained especially in animal models.

However, the EPR spectra of whole venous human blood showed a number of additional paramagnetic species with wide-line width assigned to Cu-containing proteins, such as ceruloplasmin, and narrow-line width signal with g~2 assigned to protein-centered free radicals formed in the erythrocytes. The superposition of the EPR signals from different paramagnetic centers in the same region (g~2) where the Hb-NO signal is observed made the Hb-NO quantitation problematic. The background signal of ceruloplasmin could be eliminated by separating the plasma from the erythrocytes while the free radical signal still represents a background signal that interferes with Hb-NO quantitation in vivo in human blood.

Hence, there remains a need in the art to eliminate the free radicals background in order to have an accurate measurement of NO using EPR spectroscopy. The present invention aims to provide a solution to at least the above-mentioned problem by providing a method for an accurate NO quantification in vivo in human blood.

SUMMARY

The present invention provides a method for the quantification of NO in a whole blood sample comprising the steps of collecting a whole blood sample, dividing said collected whole blood sample into at least two blood subsamples, chemically treating at least one blood subsample to at least partly reduce at least one component of said blood subsample, performing EPR measurement of said at least two blood subsamples, performing a first comparison of said chemically treated at least one blood subsample EPR measurement with the EPR measurement of at least one non-chemically treated blood subsample thereby obtaining a first comparison result.

In a preferred embodiment, the present invention provides a method further comprising the steps of:

performing a second comparison wherein said first comparison result is compared with the EPR measurement of at least one non-treated blood subsample thereby obtaining a second comparison result;

using said second comparison result for determining the NO quantity in said collected whole blood sample.

In a preferred embodiment, the present invention provides a method wherein the whole blood sample is collected in an anaerobic way. This is advantageous as it will prevent the dissociation of the in vivo formed Hb-NO complex.

In a preferred embodiment, the present invention provides a method wherein the red blood cells (RBCs or erythrocytes) of the collected blood sample are separated from the plasma of said collected whole blood sample. This is advantageous as the background signal of ceruloplasmin will be eliminated.

In a preferred embodiment, the obtained RBCs are divided in at least two blood subsamples.

In a preferred embodiment, the present invention provides a method wherein chemically treating at least one blood subsample comprises the addition of a chemical compound that will reduce at least partly the free radicals present in the treated blood subsample.

In a preferred embodiment, the present invention provides a method wherein said chemical compound comprises an antioxidant that is selected from the group of N-acetyl cysteine, $\alpha$-tocopherol, ascorbic acid and mixtures thereof such as a mixture of $\alpha$-tocopherol and ascorbic acid, a mixture of $\alpha$-tocopherol and N-acetyl cysteine, preferably said antioxidant is ascorbic acid. In a further preferred embodiment, said chemical compound consists of at least one antioxidant selected from the group of N-acetyl cysteine, $\alpha$-tocopherol, Trolox, a water soluble analog of $\alpha$-tocopherol, ascorbic acid and mixtures thereof such as a mixture of $\alpha$-tocopherol and ascorbic acid, a mixture of $\alpha$-tocopherol and N-acetyl cysteine, preferably said antioxidant is ascorbic acid.

In a more preferred embodiment, the added antioxidant has preferably a molar concentration comprised between 1 mM and 20 mM, preferably between 2 mM and 15 mM, more preferably between 3 mM and 12 mM, even more preferably around 10 mM.

In a more preferred embodiment, said at least one chemically treated blood subsample is allowed to settle before the addition of said chemical compound.

In a preferred embodiment, the present invention provides a method wherein at least one blood subsample is not chemically treated. Said at least one non-chemically treated blood subsample is physically treated by allowing said blood subsample to settle which will result in the dissociation of NO from Hb.

In another preferred embodiment, the present invention relates to a method wherein at least one blood subsample is not treated. Said at least one blood subsample is immediately frozen after being sampled from said collected whole blood sample.

In a preferred embodiment of the present invention, EPR measurements are performed for all blood subsamples.

The EPR spectrum of the at least one chemically treated blood subsample is then subtracted from the EPR spectrum of the at least one non-chemically treated blood subsample. This will result in a model EPR spectrum of free radicals specific to the collected whole blood sample. The obtained model spectrum of free radicals is then subtracted from the EPR spectrum of said at least one non-treated blood subsample. This second subtraction will provide an EPR spectrum with eliminated free radicals background and from which the quantitation of Hb-NO is performed using hyperfine component.

In a preferred embodiment, the present invention provides a method wherein said whole blood sample is a human whole blood sample.

In a second aspect, the present invention provides a kit suitable for carrying a method of NO measurement, comprising at least a winged infusion set with needle (21 G×¾"), a blood collection container, gas-tight vacuum tube with adaptor for blood sampling, a chemical solution, at least 3 Pasteur glass or plastic pipettes, at least 3 plastic syringes (1 ml) cut off at the end for subsample freezing, at least 3 small sheets of parafilm to close open end of syringe after filling and a protocol description.

In a preferred embodiment, the present invention provides a kit wherein said blood collection container is a gas-tight vacuum tube containing an anticoagulant.

In a preferred embodiment, the present invention provides a kit wherein said chemical product is an antioxidant, preferably ascorbic acid.

In a third aspect, the present invention provides a method and a kit suitable to be used for the prediction of NO related diseases and the necessary medication treatment.

The method, kit and uses provided by the invention are advantageous. The method is a minimally-invasive human approach. It delivers a precise assessment of the Hb-NO level. The invention is very attractive for providing surrogate endpoints in clinical studies for the assessment of medications efficacy or preventive strategies targeting endothelial function in very large populations of patients with risk factors for several diseases such as but not limited to pulmonary hypertension, heart failure with normal ejection fraction (HFNEF), all other forms of heart failure, atherosclerosis, all vascular ischemic diseases, diabetes, high blood pressure, dyslipidemias, metabolic syndrome, obstructive sleep apnea, all systemic inflammatory diseases. The method and kit according to the present invention provide also the possibility for monitoring the side effects of anti-cancer drugs on vascular endothelium, monitoring of blood NO in systemic inflammatory diseases and monitoring the blood NO production in response to exercise.

The method according to the invention provides a surrogate end-point in prospective clinical trials. This leads to the reduction of clinical trials costs and the reduction of medications tested for cardiovascular treatments by more precise, fast and adequate individual characterization of vascular system functionality and efficacy of medication. In this way, the method can be helpful in the development of the treatment tailoring and personalization of medicine in future perspectives.

DESCRIPTION OF THE FIGURES

FIG. 4: Linear regression analysis between the index of reactive hyperaemia response (RHI) and the Hb-NO level quantified after subtraction of model free radical signal.

FIG. 4-I: Linear regression analysis between basal Hb-NO level in RBCs isolated from venous blood, quantified after subtraction of model free radical signal, and the Framingham reactive hyperemia index (FRHI) defined as the natural logarithm of the ratio of mean post-deflation signal (in the 90 to 120-second post-deflation interval) to baseline signal in hyperemic finger normalized by the same ratio in the contra-lateral finger. Parameters of linear regression for the calibration curve were R=0.43; P<0.03; N=26 (R is a correlation coefficient; P-value is the probability that the linear correlation observed may be obtained by chance; it is considered statistically significant at a level<0.05; N, number of subjects).

FIG. 7-IA: Individual model EPR spectra of free radicals (a and a") in RBCs obtained after subtraction of the EPR spectra (b and b", correspondingly) of the subsample treated with different N-acetyl cysteine (NAC) concentrations, 5 (b) and 10 mM (b"), from the EPR spectrum of third non-treated subsample (c).

FIG. 7-IB: Comparative model EPR spectra (a and a") of free radicals obtained as described in FIG. 7-IA, but after treatment of second subsamples b and b' with different concentrations of ascorbic acid, 2 mM (b) and 10 mM (b").

FIG. 7-IC: Comparison of individual model EPR spectra of free radicals, obtained from RBCs of a single volunteer, are shown after subtraction of the EPR spectrum of the subsample treated with different antioxidants from the EPR spectrum of third non-treated subsample of the same volunteer as described in FIG. 7-IA and FIG. 7-IB. Tested antioxidants were α-tocopherol (a), Trolox (b), a water-soluble analog of α-tocopherol, and N-acetyl cysteine (c).

FIG. 8-I: Linear regression analysis between basal Hb-NO level in RBCs isolated from venous blood, quantified after subtraction of model free radical signal, and the Framingham reactive hyperemia index (FRHI) defined as the natural logarithm of the ratio of mean post-deflation signal (in the 90 to 120-second post-deflation interval) to baseline signal in hyperemic finger normalized by the same ratio in the contra-lateral finger. Parameters of linear regression were R=0.58; P<0.0001; N=50.

DETAILED DESCRIPTION OF THE INVENTION

Figure 1:
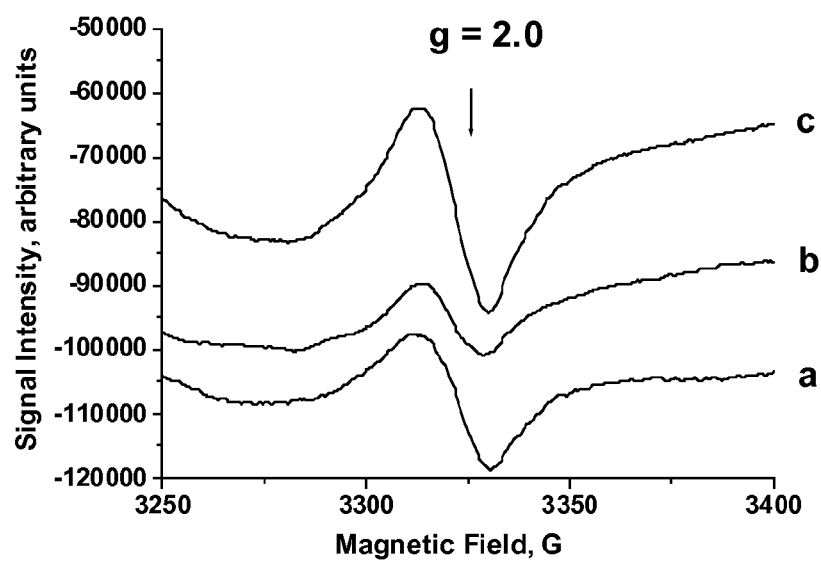
FIG. 1: Model EPR spectrum of free radicals in RBCs (a) obtained after subtraction of the EPR spectrum (b) of the second subsample of RBCs treated with ascorbic acid (AA) from the EPR spectrum (c) of the third subsample (allowed to settle and not treated with AA). The y-axis represents the intensity in arbitrary units (a.un.). The x-axis represents the magnetic field (Gauss, G) and g is a g-factor of the EPR signal.

The present invention relates to the measurement of nitric oxide (NO) amounts accumulated in blood.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

The terms "amount", "level", "concentration" and "quantity" are used herein as synonyms.

The terms "EPR measurement" and "EPR spectrum" are used herein as synonyms.

By the term "whole blood" is meant blood from which no constituent, such as red blood cells, white blood cells, plasma, or platelets, has been removed.

By the term "subsample", also referred to as "blood subsample" "RBC subsample" or "erythrocytes subsample", is meant the red blood cells obtained from the whole blood sample and divided in at least two different samples.

In the present invention, parameters of linear regression R, P and N are as follows: R is a correlation coefficient; P-value is the probability that the linear correlation observed may be obtained by chance; it is considered statistically significant at a level<0.05; and N is the number of subjects.

The present invention provides a method for the quantification of NO in a whole blood sample comprising the steps of: collecting a whole blood sample; dividing said collected whole blood sample into at least two blood subsamples; chemically treating at least one blood subsample by adding of at least one antioxidant to at least partly reduce free radicals of said blood subsample; performing EPR measurement of said at least two blood subsamples; performing a first comparison which is a subtraction of said chemically treated blood subsample EPR measurement from the EPR measurement of one non-chemically treated blood subsample thereby obtaining a first comparison result which is an EPR spectrum of protein-centered free radicals; performing a second comparison wherein said first comparison result is subtracted from the EPR measurement of another non-treated blood subsample thereby obtaining a second comparison result which is an EPR spectrum; and determining the NO quantity in said collected whole blood sample from said second comparison result using a hyperfine component. Preferably, said hyperfine component is hyperfine component of the triplet hyperfine structure of EPR spectrum of 5-coordinated nitrosylated α-Hb.

In the method according to the invention, a whole blood sample is collected directly into a gas-tight vacuum tube and immediately centrifuged. The direct collection of the whole blood sample into a gas-tight vacuum tube is an anaerobic approach that prevents the dissociation of the in vivo formed Hb-NO complex.

In a preferred embodiment, the gas-tight vacuum tube contains an anticoagulant such as heparin or sodium citrate, preferably Ethylene diamine tetra acetic acid (EDTA).

In a preferred embodiment, the whole blood sample is collected from an animal blood or from human blood. Preferably, the blood sample is venous blood, more preferably collected from the median antebrachial vein of a human.

In a preferred embodiment, centrifugation of the collected blood sample is carried out at a rotation speed comprised between 550 g and 1500 g, preferably between 650 g and 850 g, more preferably between 700 g and 800 g. Centrifugation time is comprised between 20 min and 2 min, preferably between 17 min and 5 min, more preferably between 15 min and 7 min. Centrifugation temperature is comprised between 15° C. and 1° C., preferably between 10° C. and 2° C., more preferably between 5° C. and 3° C.

In a preferred embodiment, the plasma is discarded after centrifugation of the collected whole blood sample and the erythrocytes or red blood cells (RBCs) are kept for further use.

In a preferred embodiment, the obtained erythrocytes are divided in at least two blood subsamples. These blood subsamples are collected from the bottom of the gas-tight vacuum tube using a Pasteur glass pipette. Collection of blood subsamples from the bottom of the gas-tight vacuum tube ensures the presence of erythrocytes in the collected blood subsamples. At least 0.3 ml of the obtained erythrocytes are collected in each blood subsample.

In a preferred embodiment, a first erythrocytes subsample is immediately frozen at about 77° K (−196° C.) in liquid nitrogen. This first RBCs subsample contains the in vivo formed Hb-NO.

In another preferred embodiment, a second and a third blood subsample are allowed to settle at a temperature comprised between 5° C. and 15° C., preferably between 7° C. and 13° C., more preferably between 8° C. and 11° C., even more preferably about 10° C. The said second and third blood subsamples are allowed to settle for a time comprised between 15 min and 60 min, preferably between 20 min and 45 min, more preferably between 25 min and 35 min. Allowing said second and third blood subsamples to settle will lead to the dissociation of the Hb-NO complex in said subsamples.

Afterwards, a chemical compound is added to the second blood subsample to reduce at least partly the free radicals present in said second blood subsample. The chemical compound is an antioxidant, such as but not limited to ascorbic acid.

In a preferred embodiment, the antioxidant is an ascorbic acid solution with a final molar concentration comprised between 1 mM and 20 mM, preferably between 5 mM and 15 mM, more preferably between 5 mM and 12 mM, even more preferably around 10 mM. The antioxidant is added to the blood subsample in volume proportion 1:5, 1:6, 1:7, 1:8, 1:9, 1:10, 1:11, 1:12, 1:13, 1:14 or 1:15.

Preferably, the antioxidant is added to the blood subsample in volume proportion of 1:10.

In another preferred embodiment, the second and the third blood subsamples are again allowed to settle at a temperature comprised between 5° C. and 15° C., preferably between 7° C. and 13° C., more preferably between 8° C. and 11° C., even more preferably about 10° C. Here, said second and third blood subsamples are allowed to settle for a time comprised between 30 min and 5 min, preferably between 25 min and 10 min, more preferably between 20 min and 10 min, even more preferably for about 15 min.

In a next step, the second and the third blood subsamples are frozen at about 77° K in liquid nitrogen.

In another preferred embodiment, EPR measurements are performed for all blood subsamples.

In a more preferred embodiment, a volume taken from the RBC's of each blood subsample is placed by a Pasteur glass pipette into a 1 ml plastic syringe which is cut off at the tip, the opened end of the syringe is closed with small sheet of parafilm and the subsample is immediately frozen in liquid nitrogen (−196° C.) before EPR measurements. Said volume is comprised between 0.1 ml and 0.5 ml, preferably between 0.2 ml and 0.4 ml, more preferably about 0.3 ml.

For the EPR measurement, each blood subsample is pushed out, while still frozen, from the syringe. The frozen sample is then transferred into a finger Dewar flask filled with liquid nitrogen. To reduce the EPR noise caused by nitrogen bubbling, an EPR-silent material such as but not limited to a filter paper or cotton was inserted into the gap between the frozen sample and the wall of the finger Dewar flask. The EPR measurements are carried out using an X-band EMX (Bruker Instruments Inc.) and a quartz finger Dewar under the following instrumental parameters: microwave frequency, ~9.35 GHz; modulation frequency, 100 KHz; centre field 3270 G; diapason 450 G; microwave power, 20 mW; modulation amplitude, 7 G, time constant 40.9 ms, gain $6.32 \times 10^4$; 10 scans, temperature 77K, and with control of quality factor Q. EPR measurements are carried out using an X-band MiniScope MS400 (Magnettech GmbH.) and a quartz finger Dewar under the following instrumental parameters: microwave frequency, ~9.4 GHz; modulation frequency, 100 KHz; centre field 3298 G; diapason 449 G; microwave power, 20 mW; modulation amplitude, 7 G, gain 500; 10 scans, temperature 77K.

In a preferred embodiment, the obtained EPR spectra of the different blood subsamples are used in at least two subtractions.

In a preferred embodiment, the EPR spectrum of the second chemically treated blood subsample (treated with the antioxidant) is subtracted from the EPR spectrum of the third non-chemically treated blood subsample using computer software. This first subtraction will result in an EPR model spectrum of free radicals specific to the subject from which the whole blood sample was collected.

In a preferred embodiment, the obtained EPR model spectrum of free radicals (with peak-to-peak width about 18 G) is subtracted from the EPR spectrum of the first non-treated blood subsample (containing the in vivo formed Hb-NO), using proportional coefficient obtained as a peak-to-peak amplitude ratio within the obtained model EPR spectrum of free radicals and the peak-to-peak amplitude of free radical EPR spectrum from first untreated subsample frozen immediately after centrifugation. The positions of the spectra are corrected before subtraction at g=2.0 using intrinsic standard. This second subtraction will result in an EPR spectrum from which Hb-NO is quantified in diapason 3299-3307 Gauss as a peak-to-peak amplitude of hyperfine component of the triplet hyperfine structure of EPR spectrum of 5-coordinated nitrosylated α-Hb. Magnetic field position of the component is defined for microwave frequency 9.34 GHz.

In another aspect, the invention provides a kit for carrying out the NO measurement method. The kit contains at least a winged infusion set with needle (21 G×¾") and a gas-tight vacuum tube with adaptor for blood sampling, a chemical solution, at least 4 Pasteur glass pipettes, at least 3 plastic syringes (1 ml) cut off at the end for subsample freezing, at least 3 small sheets of parafilm to close open end of syringe after filling and a protocol description.

In a preferred embodiment, the gas-tight vacuum tube provided in the kit contains an anticoagulant such as heparin or sodium citrate, preferably EDTA. In another aspect, the use of the method and kit according to the invention provides an easy approach for an accurate measurement of the NO levels in human blood. The described method can be used for the medical diagnostic of vascular diseases. It will improve the diagnostic as it allows the detection of endothelial dysfunction at a relatively early stage.

EXAMPLES

Example 1

Whole blood of one patient was collected from brachial vein directly into gas-tight vacuum tube and immediately centrifuged at 750×g for 10 minutes at 4° C.

Three subsamples of RBCs were collected after centrifugation from the bottom of the gas-tight vacuum tube using Pasteur glass pipette. 0.3 ml was collected for each subsample.

The first subsample was frozen immediately at 77° K in liquid nitrogen.

Both the second and third subsamples were allowed to settle for 30 minutes at 10° C.

Ascorbic acid (final concentration 10 mM) was added to second blood subsample after 30 minutes for free radical reduction. Ascorbic acid was added to the blood subsample in a volume proportion 1:10.

The second and third RBCs subsamples were again allowed to settle for next 15 minutes at 10° C. (finally 45 minutes after centrifugation) and then both blood subsamples were frozen in liquid nitrogen (77° K).

EPR measurements of the three blood subsamples were performed: 0.3 ml of each blood subsample were placed by Pasteur glass pipette into a 1 ml plastic syringe, which was cut off at the tip, closed with small sheet of parafilm and immediately frozen in liquid nitrogen. The blood subsamples (still frozen) were pushed out from the syringe and transferred into the finger Dewar flask filled with liquid nitrogen. The instrumental parameters for EPR measurements by X-band EMX (Bruker Instruments Inc.) were as follows: microwave frequency, ~9.33 GHz; modulation frequency, 100 KHz; centre field 3270 G; diapason 450 G; microwave power, 20 mW; modulation amplitude, 7 G, time constant 40.9 ms, gain $6.32 \times 10^4$; 10 scans. Three EPR spectra were obtained.

Subtraction analysis of the obtained spectra was carried out 2 times:

a) the spectrum of the chemically treated RBCs subsample (second subsample treated with ascorbic acid) was subtracted from the spectrum of the non-chemically treated blood subsample (third subsample). A model spectrum of free radicals specific to the patient was obtained as illustrated in FIG. 1.

FIG. 1: Model signal of free radicals (a) obtained after first subtraction. The highest EPR spectrum (c) was obtained from the third non-chemically treated blood subsample. The EPR spectrum in the middle (b) was obtained from the second chemically treated blood subsample. The lowest EPR spectrum (a) is the model spectrum of free radicals specific to the patient from which the whole blood sample was collected.

b) the obtained model spectrum of free radicals was subtracted from the EPR spectrum of the non-treated blood subsample (first subsample) using proportional coefficient (FIG. 2B and FIG. 3B). A final EPR spectrum was obtained as shown for different volunteers (k in FIG. 2B and k' in FIG. 3B).

The final obtained spectrum was used for the quantification of Hb-NO using high-field hyperfine (hf) structure of 5-coordinated nitrosylated α-Hb as a peak-to-peak amplitude of hf component of the triplet hyperfine structure of EPR spectrum in diapason 3299-3307 Gauss at microwave frequency~9.34 GHz. The spectrum observed after addition of NO donor to isolated RBCs in vitro was used as an etalon control as shown in FIG. 2 and FIG. 3, i and i' respectively.

Figure 2:
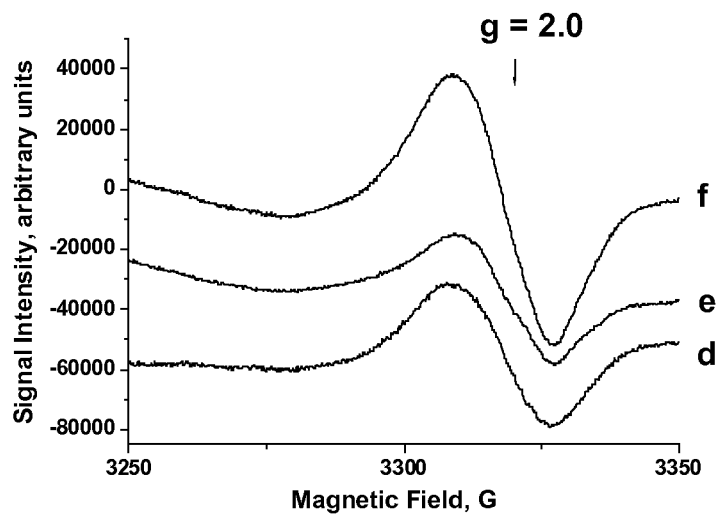
FIG. 2: Example of double subtraction (volunteer 1). The y-axis represents the intensity in arbitrary units. The x-axis represents the magnetic field, G. A. Individual model spectrum of free radicals (with g-factor~2) in RBCs (d) obtained after subtraction of the EPR spectrum (e) of the second subsample (RBCs treated with AA) from the EPR spectrum (f) of the third subsample not treated with AA. B. EPR spectrum of RBCs of healthy human volunteer 1 (k), presented as a high field component, after final subtraction of the model EPR spectrum of free radicals (d) from the EPR spectrum of the first subsample (h) frozen immediately after sampling; a high field component of etalon spectrum of Hb-NO is presented in (i).
Figure 2:
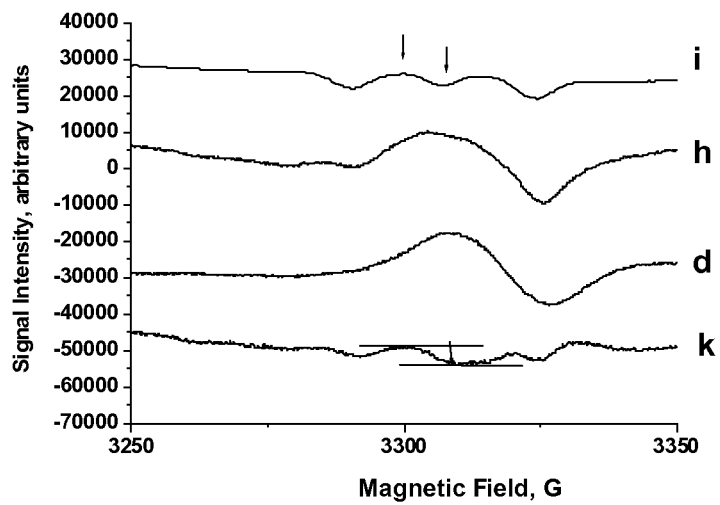

FIG. 2: Example of double subtraction (volunteer 1):
A. Individual model spectrum of free radicals in RBCs (d) obtained after subtraction of the EPR spectrum (e) of the second subsample (RBCs treated with AA) from the EPR spectrum (f) of the third subsample (allowed to settle and not treated with AA). B. EPR spectrum of RBCs of healthy human volunteer 1 (k), presented as a high field component, after final subtraction of the model EPR spectrum of free radicals (d) divided by the proportional coefficient (K=2.4 in this experiment) from the EPR spectrum of the first subsample (h) frozen immediately after /sampling. A peak-to-peak amplitude of $2^{nd}$ hf component of the triplet hyperfine structure of EPR spectrum is A=4120 a.un. (volunteer 1). Signal of 5-coordinated nitrosylated α-Hb in RBCs incubated with nitric oxide donor in vitro (spectrum Hb-NO) is presented as an etalon in a 1:6 scale for comparison (i).

Figure 3:
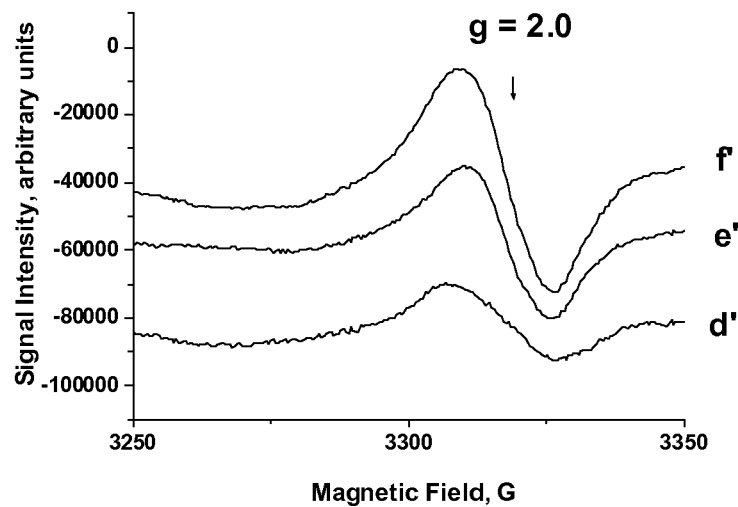
FIG. 3: Example of double subtraction (volunteer 2). The y-axis represents the intensity in arbitrary units. The x-axis represents the magnetic field G. A. Individual model spectrum of free radicals (with g-factor~2) in RBCs (d') obtained after subtraction of the EPR spectrum (e') of the second subsample (RBCs treated with AA) from the EPR spectrum (f') of the third subsample not treated with AA. B. EPR spectrum of RBCs of healthy human volunteer 2 (k'), presented as a high field component, after final subtraction of the model EPR spectrum of free radicals (d') from the EPR spectrum of the first subsample (h) frozen immediately after sampling; a high field component of etalon spectrum of Hb-NO is presented in (I').
Figure 3:
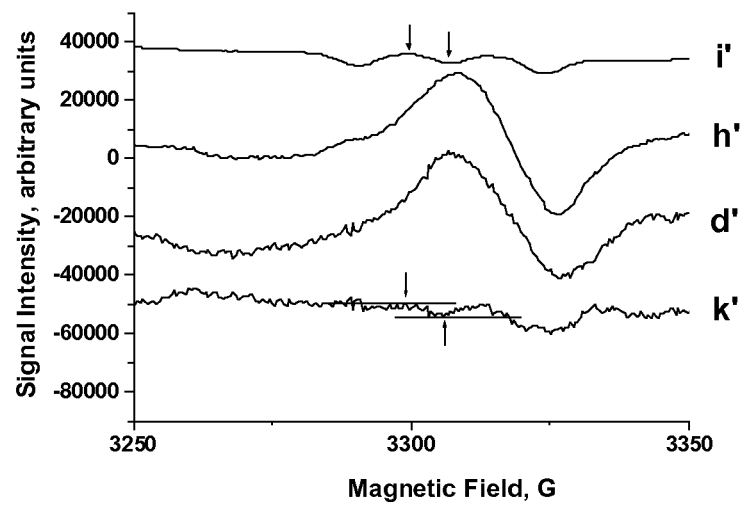

FIG. 3: Example of double subtraction (volunteer 2):
A. Individual model spectrum of free radicals in RBCs (d') obtained after subtraction of the EPR spectrum (e') of the second subsample (RBCs treated with AA) from the EPR spectrum (f') of the third subsample (allowed to settle and not treated with AA). B. EPR spectrum of RBCs of healthy human volunteer 2 (k'), presented as a high field component, after final subtraction of the model EPR spectrum of free radicals (d') divided by the proportional coefficient (K=0.52 in this experiment) from the EPR spectrum of first subsample (h') frozen immediately after sampling. A peak-to-peak amplitude of $2^{nd}$ hf component of the triplet hyperfine structure of EPR spectrum is A=2650 a.un. (volunteer 2). Signal of 5-coordinated nitrosylated α-Hb in RBCs incubated with nitric oxide donor in vitro (spectrum Hb-NO) is presented as an etalon in a 1:6 scale for comparison (i').

Example 2

To further show the effectiveness and applicability of the method of the present invention, wherein erythrocyte Hb-NO level is used for characterization of human endothelial function, a correlation between index of reactive hyperaemia response (RHI) and level of Hb-NO was studied. This was performed in RBCs from venous blood collected from the same arm that was used for RHI test. Standard RHI test follows changes of pulsatile volume of distal digit by measurement of peripheral arterial tone (PAT) amplitude before and after arterial occlusion of the arm for 5 minutes. EndoPat2000 device (Itamar Medical Inc.) was used to perform the test. The device was previously validated in large populations to assess PAT signal.

The study was performed in a group of 24 healthy volunteers (27+/−1 years old, 46% female). Three volunteers were excluded from the current study due to the poor signal quality or the individual unusual response to occlusion (high sport activity or abnormal reactivity of control arm). Free radicals were inhibited by ascorbic acid 10 mM in vitro according to the present invention's protocol in 57% of samples isolated from blood of the volunteers. A linear correlation was observed between the Hb-NO basal level circulating in RBCs of venous blood and RHI measured at the same time in parallel with blood sampling from the same arm. FIG. 4 shows the linear regression analysis between the index of reactive hyperaemia response (RHI), calculated automatically by the software of EndoPat2000 as a ratio of mean post-deflation signal (in the 90 to 120-second post-deflation interval) to baseline signal in hyperemic finger normalized by the same ratio in the contra-lateral finger and multiplied by a baseline correction factor (K=0.52397×log (mean baseline amplitude)−0.2), and the level of Hb-NO quantified after subtraction of the model of free radical signal, obtained from difference between EPR signals of RBCs treated or not with ascorbic acid in vitro as described above. The straight line represents the result of least-squares regression. Quantitation of the Hb-NO level was performed using the calibration curve obtained from the EPR signals of Hb-NO formed in RBCs treated with known concentration of nitrite in presence of $Na_2S_2O_4$ in anaerobic condition (37° C.; 1% of $O_2$; RUSKINN workstation INVIVO$_2$400). The parameters of linear regression were correlation coefficient R=0.63, and P=0.029 (N=12).

Another study was performed in a group of 53 healthy volunteers (27.7+/−0.8 years old, 54% female). Three volunteers were excluded from the current study due to the poor signal quality or the individual unusual response to occlusion (high sport activity or abnormal reactivity of control arm). Free radicals were inhibited by ascorbic acid 10 mM in vitro according to the present invention's protocol in 53% of samples isolated from blood of the different volunteers. A linear correlation was observed between the Hb-NO basal level circulating in RBCs of venous blood and FRHI measured at the same time in parallel with blood sampling from the same arm. FIG. 4-I shows the linear regression analysis between the Framingham index of reactive hyperaemia response (FRHI), calculated automatically by the software of EndoPat2000, and the level of Hb-NO quantified after subtraction of the model of free radical signal, obtained from the difference between EPR signals of RBCs treated or not with ascorbic acid in vitro as described above in the group comprising 26 healthy volunteers. The Framingham reactive hyperemia index (FRHI) is defined as the natural logarithm of the ratio of mean post-deflation signal (in the 90 to 120-second post-deflation interval) to the baseline signal in hyperemic finger normalized by the same ratio in the contra-lateral finger.

Figure 5:
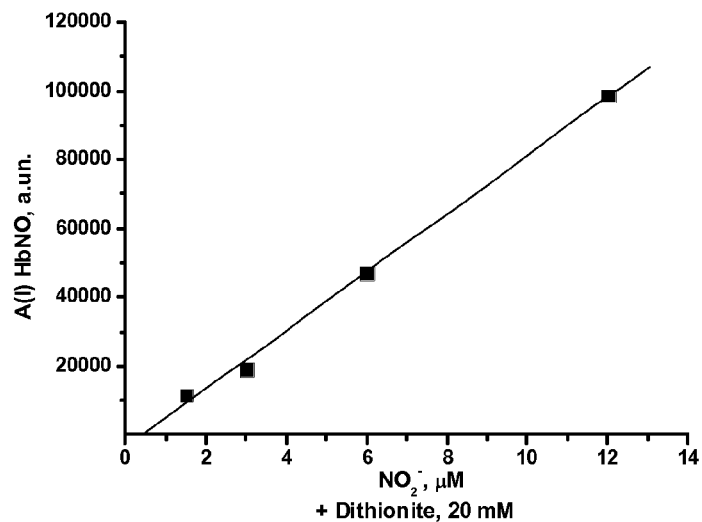
FIG. 5: (A) Calibration curve for quantitation of the Hb-NO level. (B) EPR signals of Hb-NO formed in intact RBCs treated with known concentration of nitrite in presence of $Na_2S_2O_4$ in anaerobic condition.
Figure 5:
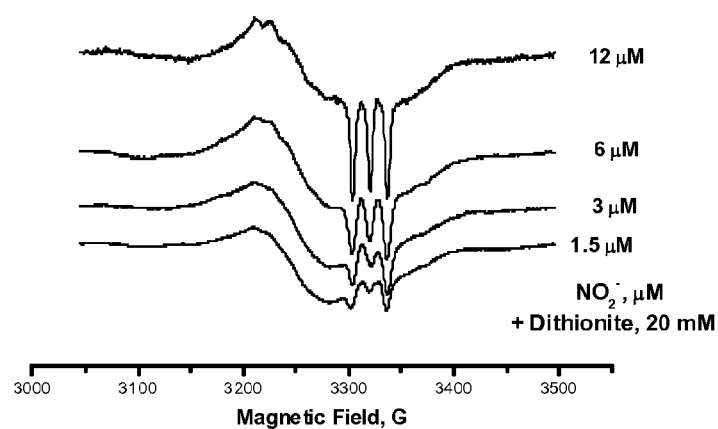

The calibration curve used for quantification of amount of Hb-NO, formed in erythrocytes, is shown in FIG. 5. The calibration curve (A) was obtained from the EPR signals of Hb-NO (B) formed in intact RBCs treated with known concentration of nitrite in presence of $Na_2S_2O_4$ (20 mM) in anaerobic condition (1% of $O_2$; RUSKINN workstation INVIVO$_2$400; 37° C.). In these anaerobic conditions nitric oxide, formed in equimolar ratio from nitrite after reduction by $Na_2S_2O_4$; proportionally interacts with deoxy-haemoglobin. Parameters of linear regression for the calibration curve were R=0.999 and P=0.001 for N=4. The EPR signals were standardized by comparison of the spectrum intensity after double integration with intensity of known stable standard, a buffer solution of Cu(EDTA) frozen in 30% of glycerol at concentration 50 and 100 μM.

Figure 6:
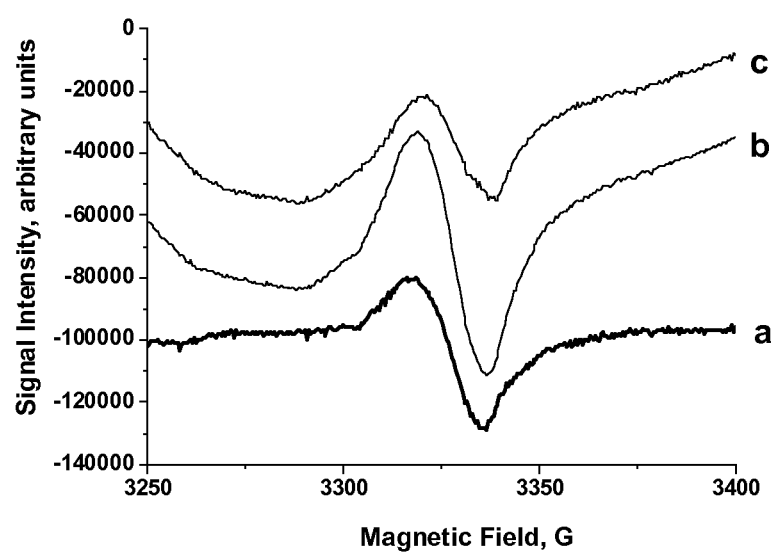
FIG. 6: Individual model EPR spectrum of free radicals (a) in RBCs with prooxidant profile was obtained after inverse subtraction of the EPR spectrum of the third non-treated subsample (c) from the EPR spectrum of second subsample treated with AA (b).

Individual redox properties were found for RBCs isolated from blood of different human volunteers. It was observed that the redox reaction between RBC free radicals and ascorbic acid, added in vitro, can vary for different individuals as well as the basal blood EPR signal of free radicals, formed predominantly in the RBCs. Prooxidant activity of ascorbic acid at the same concentration and time of incubation was found in RBCs isolated from blood in 47% of the volunteers. The signal of free radicals was increased in these samples after addition of ascorbic acid (10 mM, 15 min). In such cases, inverse subtraction can be used for two subsamples obtained before and after incubation with solution of antioxidant. FIG. 6 shows individual model EPR spectrum of free radicals (a) in RBCs obtained after inverse subtraction of the EPR spectrum of the non-treated subsample (c) from the EPR spectrum of third subsample treated with ascorbic acid (10 mM) (b) in RBCs with prooxidant profile.

Example 3

Figure 7:
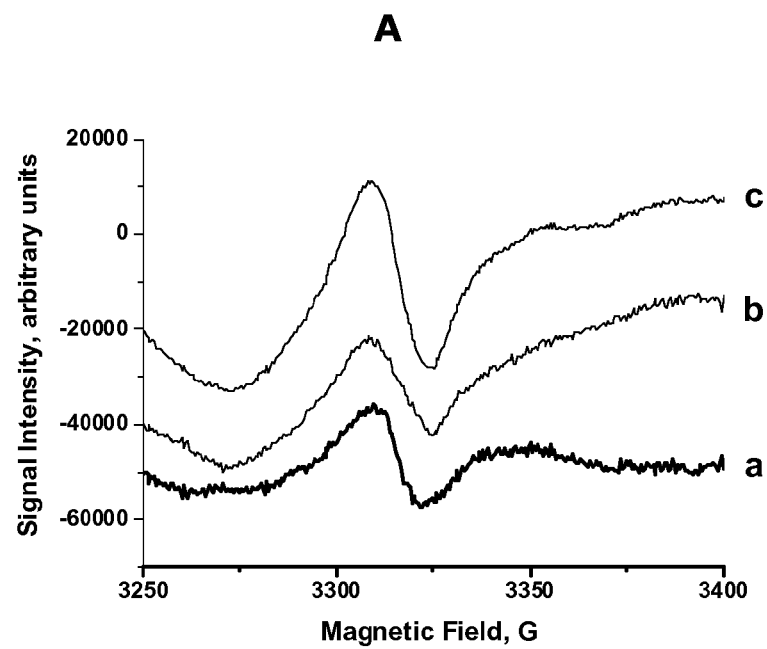
FIG. 7: A. Individual model EPR spectrum of free radicals (a) in RBCs obtained after subtraction of the EPR spectrum (b) of the subsample treated with N-acetyl cysteine, from the EPR spectrum of third non-treated subsample (c). B. Individual model EPR spectrum of free radicals (a) in RBCs obtained after subtraction of the EPR spectrum (b) of the subsample treated with α-tocopherol (4 mM) from the EPR spectrum of third non-treated subsample (c).
Figure 7:
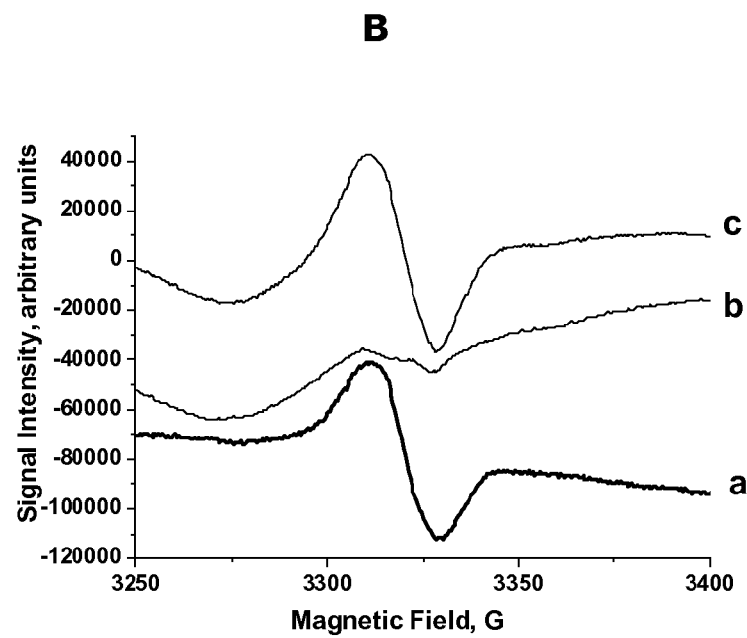

Redox activity of various antioxidants was studied in isolated RBCs. The obtained results showed that N-acetyl cysteine (NAC, 5-10 mM); α-tocopherol (4-10 mM); a mixture (1:1) of α-tocopherol (4 mM):ascorbic acid (10 mM) and of α-tocopherol (4 mM):N-acetyl cysteine (10 mM), can substitute ascorbic acid to inhibit in vitro free radicals formed in RBCs. The results are shown in FIG. 7, wherein FIG. 7A shows individual model EPR spectrum of free radicals (a) in RBCs obtained after subtraction of the EPR spectrum (b) of the subsample treated with N-acetyl cysteine (NAC, 10 mM), from the EPR spectrum of third non-treated subsample (c). FIG. 7B shows individual model EPR spectrum of free radicals (a) in RBCs obtained after subtraction of the EPR spectrum (b) of the subsample treated with α-tocopherol (4 mM) from the EPR spectrum of third non-treated subsample (c).

Figure 8:
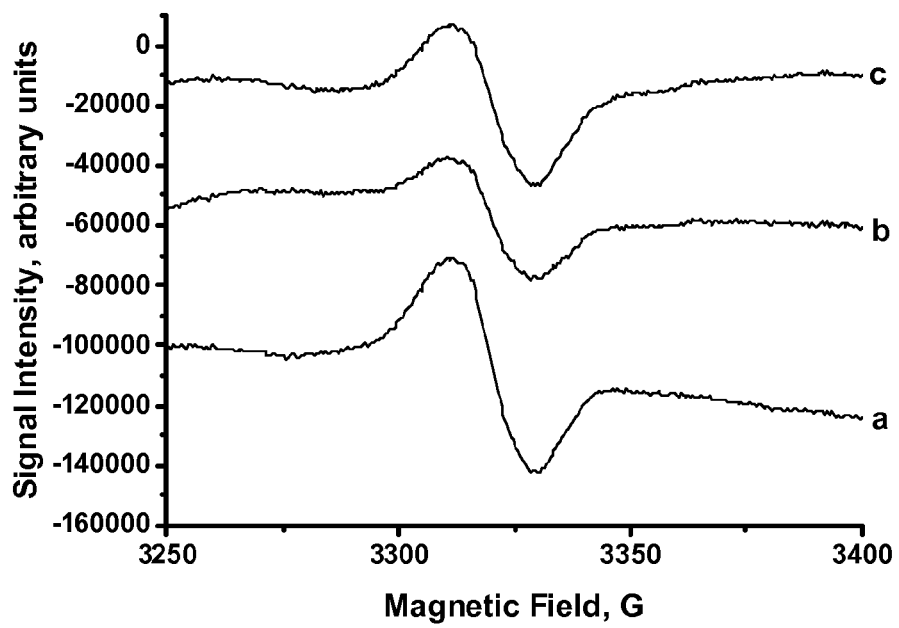
FIG. 8: Linear regression analysis between the index of reactive hyperaemia response (RHI) and the Hb-NO level, quantified after subtraction of model free radical signal.
Figure 8:
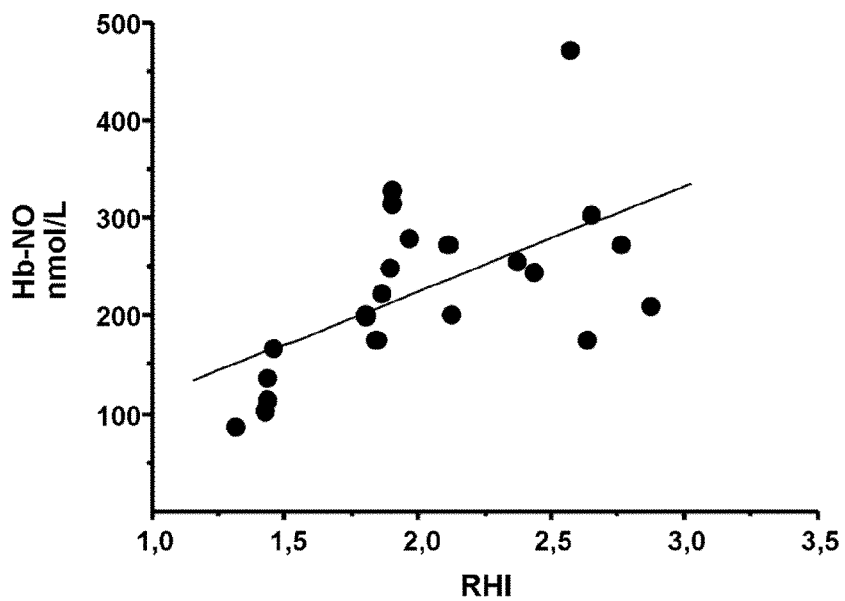

The correlation results between Hb-NO level in RBCs and EndoPAT signal, observed for this group are shown in FIG. 8. Parameters of linear regression were R=0.6; P=0.005 (N=21). FIG. 8 shows the linear regression analysis between the index of reactive hyperaemia response (RHI), calculated automatically by the EndoPat2000 software, and the level of Hb-NO, quantified after subtraction of model free radical signal obtained with antioxidant treatment of RBCs in vitro as described above. The straight line represents the result of least-squares regression. Quantitation of the level of Hb-NO was done using calibration curve (FIG. 5A) obtained from the EPR Hb-NO signals of RBCs treated with known concentration of nitrite in presence of $Na_2S_2O_4$ in anaerobic condition (37° C.; 1% of $O_2$; RUSKINN workstation INVIVO$_2$400).

Redox activity of various antioxidants at different concentrations was also studied in isolated RBCs. The obtained results showed that N-acetyl cysteine (NAC) with a concentration of 5-10 mM; α-tocopherol with a concentration of 4 mM; Trolox which is a water-soluble analog of α-tocopherol with a concentration of 1.7 mM; a mixture (1:1) of α-tocopherol with a concentration of 4 mM:ascorbic acid with a concentration of 10 mM and/or a mixture (1:1) of α-tocopherol with a concentration of 4 mM:N-acetyl cysteine with a concentration of 10 mM, can substitute ascorbic acid to inhibit in vitro free radicals formed in RBCs. The results are shown in FIG. 7-IA showing individual model EPR spectra of free radicals (a and a') in RBCs obtained after subtraction of the EPR spectrum of the subsample treated with different N-acetyl cysteine (NAC) concentrations, 5 mM for subsample (b) and 10 mM for subsample (b'), from the EPR spectrum of third non-treated subsample (c). FIG. 7-IB shows comparative model EPR spectra of free radicals obtained by using a subsample treatment with different concentrations of ascorbic acid (2 and 10 mM).

FIG. 7-IC shows a comparison of different antioxidant effect. The model EPR spectra of free radicals in RBCs obtained from a single volunteer after subtraction of the EPR spectrum of the subsample treated with different antioxidants from the same EPR spectrum of third non-treated subsample. The effect of α-tocopherol 4 mM is shown in a; effect of Trolox which is a water-soluble analog of α-tocopherol 1.7 mM is shown in b and effect of N-acetyl cysteine 10 mM is shown in c. All model spectra, being divided by correspondent proportional scale factor, were used for subtraction. Proportional scale factors were k=1.33 (a); 0.75 (b); 0.96 (c) related to intensity of free radical signal in first non-treated subsample.

The correlation results between Hb-NO level in RBCs and EndoPAT signal, observed for data from all group (N=50) are shown in FIG. 8-I. Parameters of linear regression were R=0.58; P<0.0001. FIG. 8-I shows the linear regression analysis between the Framingham index of reactive hyperaemia response (FRHI), calculated automatically by the EndoPat2000 software, and the level of Hb-NO, quantified after subtraction of model free radical signal obtained with antioxidant treatment of RBCs in vitro as described above.

Example 4

Test of NO formation in circulation determined by the accumulation of Hb-NO in RBCs obtained from a volunteer after in vivo treatment with glyceryl trinitrate (GTN).

RBCs were isolated as described previously from blood of a volunteer 2 minutes before and 2 minutes after acute GTN administration (sublingual GTN spray, 2 doses, 0.4 mg/dose). Hb-NO level was increased to nearly twice the basal level after 2 minutes of the acute in vivo GTN administration.

Figure 9:
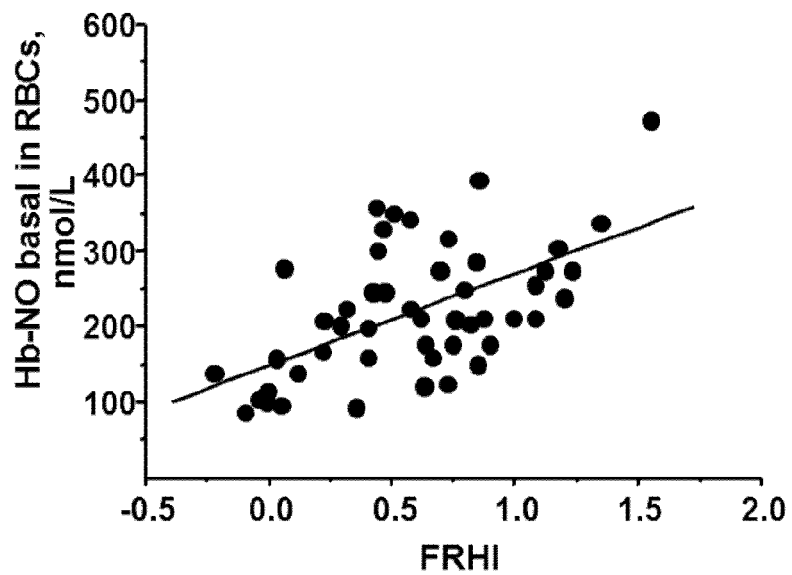
FIG. 9: Quantitative detection of NO formation in circulation, measured as accumulation of Hb-NO in RBCs, obtained from a volunteer after in vivo treatment with sublingual glyceryl trinitrate (GTN).
Figure 9:
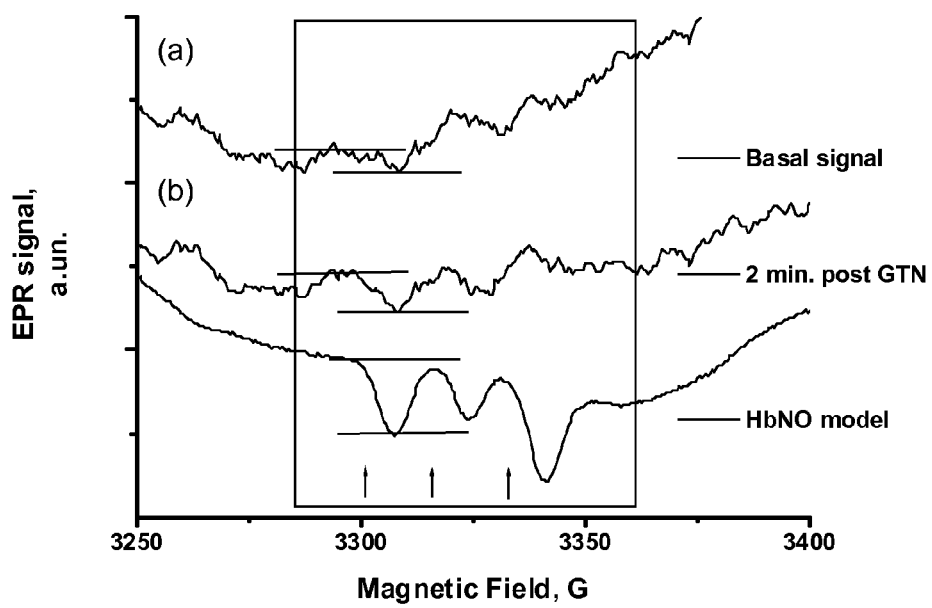

FIG. 9 shows the final EPR spectra of RBCs (gain=6.2× $10^4$), isolated before (a) and after (b) GTN sublingual administration (in spray, 2 doses, 0.4 mg/dose), shown after subtraction of the model spectrum of free radicals, divided by the correspondent proportional scale factor, from the EPR spectrum of the initial sample frozen immediately. Typical EPR spectra of RBCs, frozen after incubation under low $O_2$ level with the NO-donor, Dea-NONOate (1,1-Diethyl-2-hydroxy-2-nitroso-hydrazine, 50 μmol/L; gain=3.1×$10^4$) are shown at the bottom of the figure (Hb-NO model) for comparison. Peak-to-peak amplitude of hf component of the Hb-NO triplet structure attributed to 5-coordinated nitrosylated α-Hb was used for quantitation. Spectra are recorded using Bruker spectrometer (X-band, microwave frequency~9.35 GHz) with the following setting: modulation frequency, 100 kHz; microwave power (MP), 20 mW; modulation amplitude (MA), 7 mT; 10 scans, 77K.

Example 5

Test of NO formation in circulation determined by the accumulation of Hb-NO in RBCs, obtained from volunteer after five-minute exercise (stairs climbing).

Figure 10:
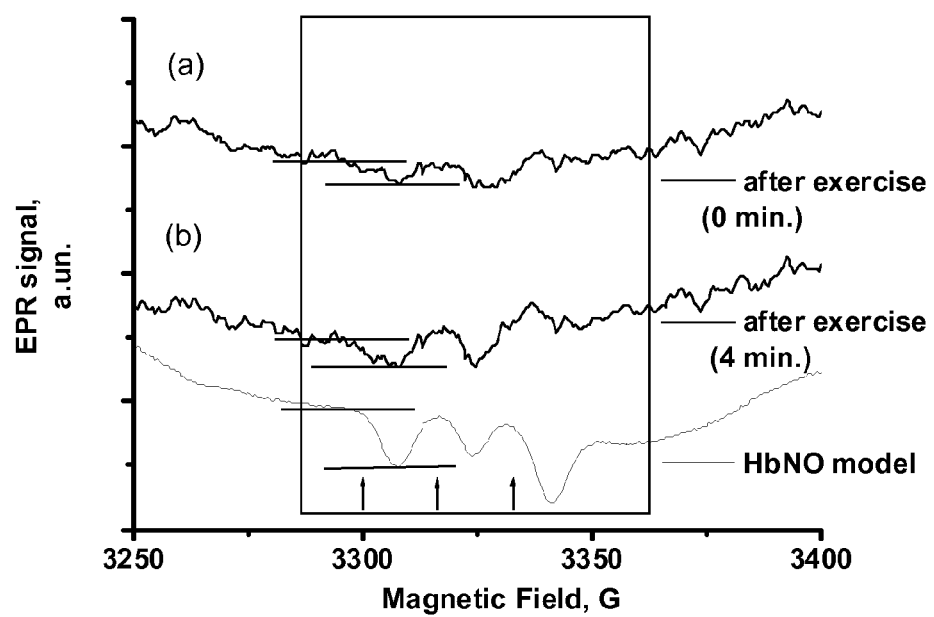
FIG. 10: Quantitative detection of NO formation in circulation, measured as the accumulation of Hb-NO in RBCs, obtained from a volunteer after five-minute exercise (stair climbing).

FIG. 10 shows the final EPR spectra of RBCs (gain=6.2× $10^4$), isolated immediately (a) and 4 min. (b) after a five-minute exercise, shown after subtraction of the model spectrum of free radicals, divided by the correspondent proportional scale factor, from the EPR spectrum of the initial sample. Typical EPR spectra of RBCs, frozen after incubation under low $O_2$ level with the NO-donor, Dea-NONOate (50 µmol/L; gain=$3.1 \times 10^4$) are shown at the bottom of the figure for comparison. Peak-to-peak amplitude of hf component, of the Hb-NO triplet structure attributed to 5-coordinated nitrosylated α-Hb was used for quantitation. Spectra are recorded using Bruker spectrometer (X-band, microwave frequency~9.35 GHz) with setting: modulation frequency, 100 kHz; microwave power (MP), 20 mW; modulation amplitude (MA), 7 mT; 10 scans, 77K.

Example 6

Test of NO formation in circulation determined as the accumulation of Hb-NO in RBCs, obtained from patient using an X-band MiniScope MS400 (Magnettech GmbH.) and a quartz finger Dewar et the temperature 77K.

Figure 11:
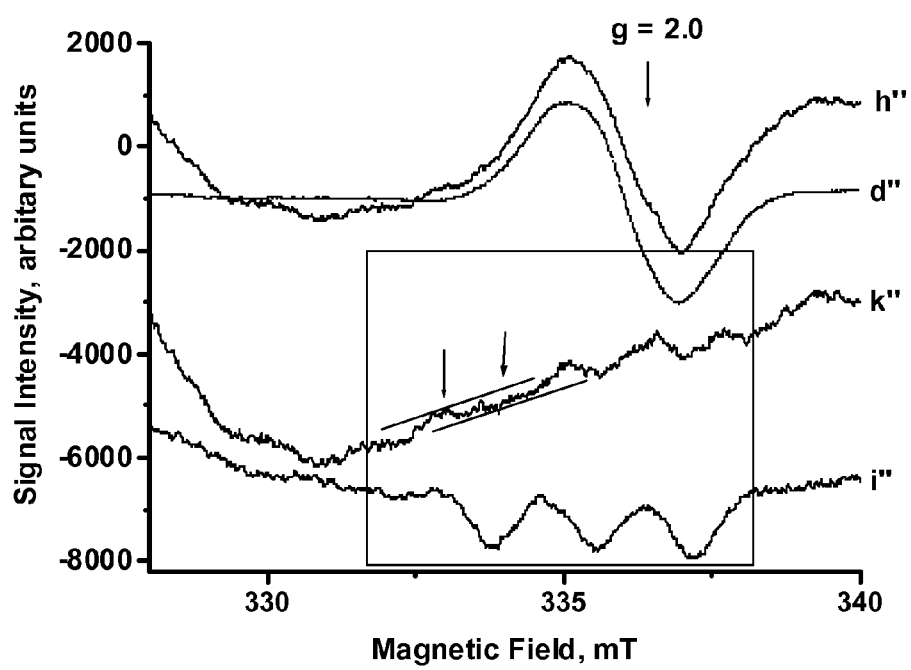
FIG. 11: Final EPR spectra of RBCs (k"), recorded using EPR spectrometer MiniScope MS400 (Magnettech GmbH., X-band) after subtraction of the model spectrum of free radicals (d", divided by the correspondent proportional scale factor, K=3.5) from the EPR spectrum of the initial sample (h"). Typical EPR spectra of RBCs (I"), frozen after incubation under low $O_2$ level with the NO-donor system as described in FIG. 5, are shown at the bottom of the figure for comparison.

FIG. 11 shows the final EPR spectra of RBCs (k", gain=500×1.5) after subtraction of the model spectrum of free radicals (d", divided by the correspondent proportional scale factor, K=3.5) from the EPR spectrum of the initial sample (h", gain=500). Typical EPR spectra of RBCs, frozen after incubation under low $O_2$ level with the NO-donor system as described in FIG. 5 are shown at the bottom of the figure for comparison (gain=500:4). Peak-to-peak amplitude of hf component, of the Hb-NO triplet structure attributed to 5-coordinated nitrosylated α-Hb was used for quantitation. Spectra are recorded using EPR spectrometer MiniScope MS400 (Magnettech GmbH., X-band) microwave frequency~9.4 GHz with setting: modulation frequency, 100 kHz; microwave power (MP), 20 mW; modulation amplitude (MA), 7 mT; 10 scans, 77K.

Example 7

Figure 12:
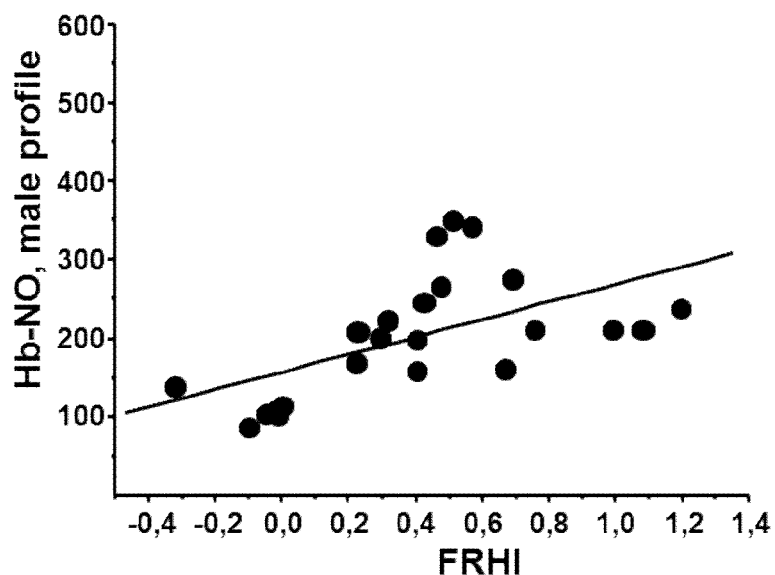
FIG. 12: Linear regression analysis between basal Hb-NO level in RBCs isolated from venous blood of male (A) and female (B) subjects and FRHI (Framingham reactive hyperemia index) calculated by EndoPat software. Parameters of linear regression were R=0.57; P<0.005; N=23 and R=0.55; P<0.005; N=27 respectively.
Figure 12:
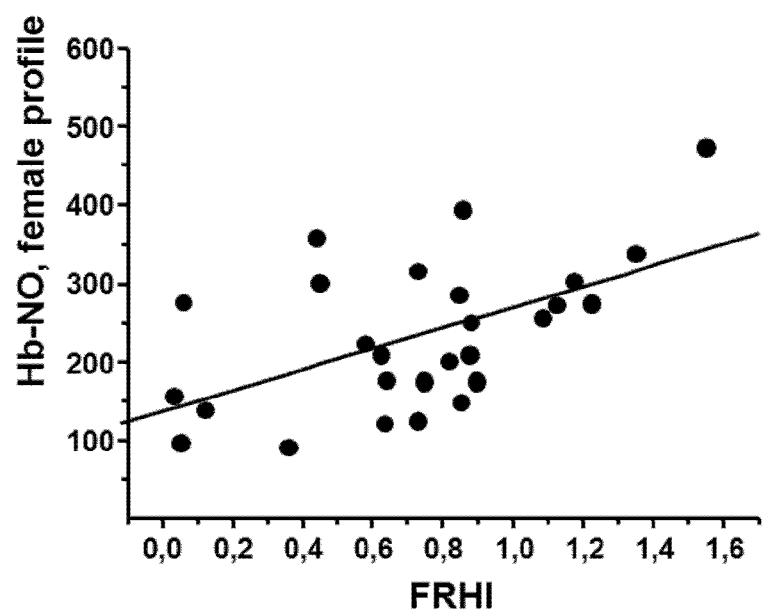

Correlations of Hb-NO levels with FRHI are compared between healthy male and female volunteers, as shown in FIG. 12 (A, male profile and B, female profile). A significant difference (P<0.05) in Hb-NO levels was observed between male (201±19 nmol/L, N=23) and female volunteers (279±29 nmol/L, N=12). Said female volunteers did not take contraceptive pills.

What is claimed is:

1. A method for the quantification of nitric oxide (NO) in a whole blood sample comprising the steps of:
   collecting a whole blood sample from an individual human subject, wherein said blood sample is collected directly into a gas-tight vacuum tube,
   centrifuging the collected sample and discarding the plasma after said centrifugation thereby maintaining erythrocytes,
   dividing said erythrocytes into three blood subsamples, wherein a first subsample is immediately frozen, and wherein said first subsample comprises in-vivo formed Hemoglobin-NO and protein-centered free radicals,
   allowing a second and a third blood subsample to settle at a temperature between 5 and 15° C. for 15 to 60 min thereby dissociating Hemoglobin-NO complexes,
   chemically treating the second blood subsample by adding of at least one antioxidant to at least partly reduce free radicals of said second subsample,
   allowing the second subsample and the remaining non-chemically treated and non-frozen third blood subsample to settle again at a temperature between 5 and 15° C. thereby further dissociating Hemoglobin-NO complexes,
   freezing the second and third subsamples,
   performing electron paramagnetic resonance (EPR) measurement of said three frozen blood subsamples,
   performing a first comparison which is a subtraction of the chemically treated second blood subsample EPR measurement from the EPR measurement of the third non-chemically treated blood subsample thereby obtaining a first comparison result which is contains an EPR spectrum of protein-centered free radicals specific to the human subject from which the whole blood sample was collected,
   performing a second comparison wherein said first comparison result is subtracted from the EPR measurement of the first blood subsample which was frozen thereby obtaining a second comparison result which is an EPR spectrum of Hemoglobin-NO with eliminated EPR signal of protein-centered free radicals,
   determining the NO quantity in said collected whole blood sample by quantification of the hemoglobin-nitric oxide adducts (Hb-NO) from the EPR spectrum obtained from the second comparison.

2. A method according to claim 1, wherein said antioxidant is selected from the group consisting of N-acetyl cysteine, α-tocopherol, Trolox, ascorbic acid and mixtures thereof.

3. A method according to claim 1, wherein the added antioxidant has a molar concentration between 1 mM and 20 mM.

4. A method according to claim 1, wherein said blood subsamples comprise at least separated red blood cells.

5. A kit suitable for carrying a method according to claim 1, comprising at least a blood collection container and a chemical product which is an antioxidant.

6. A kit according to claim 5, wherein said blood collection container is a gas tight vacuum tube containing an anticoagulant.

7. A kit according to claim 5, wherein said antioxidant is selected from the group consisting of N-acetyl cysteine, a-tocopherol, Trolox, ascorbic acid and mixtures thereof.

8. A method of predicting NO related diseases and the necessary medication treatment comprising quantifying the NO in a whole blood sample according to claim 1.

9. A method according to claim 2, wherein the added antioxidant has a molar concentration between 1 mM and 20 mM.

10. A method according to claim 2, wherein said hyperfine component is hyperfine component of the triplet hyperfine structure of EPR spectrum of 5-coordinated nitrosylated α-Hb.

11. A method according to claim 3, wherein said hyperfine component is hyperfine component of the triplet hyperfine structure of EPR spectrum of 5-coordinated nitrosylated α-Hb.

12. A method according to claim 2, wherein the first blood subsample used in said second comparison is frozen, in liquid nitrogen, after being collected from said whole collected blood sample.

13. A method according to claim 3, wherein the first blood subsample used in said second comparison is frozen, in liquid nitrogen, after being collected from said whole collected blood sample.

14. A method according to claim 2, wherein said antioxidant is a mixture of a-tocopherol and ascorbic acid, a mixture of a-tocopherol and N-acetyl cysteine or a mixture of N-acetyl cysteine and ascorbic acid.

15. A method according to claim 14, wherein said antioxidant is a mixture of N-acetyl cysteine and ascorbic acid.

16. A kit according to claim 7, wherein said antioxidant is a mixture of a-tocopherol and ascorbic acid, a mixture of a-tocopherol and N-acetyl cysteine or a mixture of N-acetyl cysteine and ascorbic acid.

17. A kit according to claim 16, wherein said antioxidant is a mixture of N-acetyl cysteine and ascorbic acid.

* * * * *

UNITED STATES PATENT AND TRADEMARK OFFICE
CERTIFICATE OF CORRECTION

PATENT NO.         : 9,696,324 B2
APPLICATION NO.    : 14/367209
DATED              : July 4, 2017
INVENTOR(S)        : Jean-Luc Balligand et al.

It is certified that error appears in the above-identified patent and that said Letters Patent is hereby corrected as shown below:

In the Specification

In Column 5 at Line 30, Change "(I')." to --(i').--.

In Column 5 at Line 66, Change "a")" to --a')--.

In Column 5 at Line 67, Change "b"," to --b',--.

In Column 6 at Line 2, Change "(b")," to --(b'),--.

In Column 6 at Line 4, Change "a")" to --a')--.

In Column 6 at Line 7, Change "(b")." to --(b').--.

In Column 6 at Line 42, Change "(I")," to --(i"),--.

In Column 11 at Line 28, Change "/sampling." to --sampling.--.

In Column 12 at Line 61, Change "$Na_2S_2O_4$;" to --$Na_2S_2O_4$,--.

In the Claims

In Column 15 at Line 60, In Claim 1, before "at least one" delete "of".

In Column 16 at Line 7 (approx.), In Claim 1, after "which" delete "is".

In Column 16 at Line 39, In Claim 7, change "a-" to --α- --.

In Column 16 at Line 63, In Claim 14, change "a-" to --α- --.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*

In Column 16 at Line 64, In Claim 14, change "a-" to --α- --.

In Column 17 at Line 2, In Claim 16, change "a-" to --α- --.

In Column 17 at Line 3, In Claim 16, change "a-" to --α- --.